United States Patent [19]

Grohe et al.

[11] 4,237,143
[45] Dec. 2, 1980

[54] COMBATING FUNGI WITH 2-METHYLENE-3-SUBSTITUTED-4,5-BIS-TRIFLUORO-METHYL IMINO-THIAZOLIDINES

[75] Inventors: Klaus Grohe, Odenthal; Hans-Joachim Scholl, Cologne; Volker Paul, Solingen; Wilhelm Brandes, Leichlingen; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 9,564

[22] Filed: Feb. 5, 1979

[30] Foreign Application Priority Data

Feb. 25, 1978 [DE] Fed. Rep. of Germany ....... 2808227

[51] Int. Cl.$^3$ .......................................... C07D 277/04
[52] U.S. Cl. ................................... 424/270; 544/133; 548/191
[58] Field of Search ................... 260/306 T; 424/270; 544/133; 548/191

[56] References Cited

U.S. PATENT DOCUMENTS 3,895,020  7/1975  Scholl et al. .................... 424/270
3,899,584  8/1975  Scholl et al. .................... 424/270

Primary Examiner—Nicholas S. Rizzo
Attorney, Agent, or Firm—Sprung, Felfe, Horn, Lynch & Kramer

[57] ABSTRACT

2-Methylene-3-substituted-4,5-bis-trifluoromethylimino-thiazoldines of the formula $$CF_3-N=\underset{R^1-N\underset{\underset{R^2\diagup\diagdown R^3}{\overset{\|}{C}}}{\diagdown S\diagup}}{\phantom{xx}}=N-CF_3$$

in which

R$^1$ represents optionally substituted alkyl, optionally substituted alkenyl, optionally substituted alkynyl, optionally substituted cycloalkyl, optionally substituted aryl, aralkyl, it being possible for the last-mentioned group to be substituted on the alkyl radical, or an amino group —NR$^4$R$^5$, wherein R$^4$ and R$^5$ may be identical or different, each represent optionally substituted alkyl, or R$^4$ and R$^5$ together with the connecting nitrogen atom and optionally one or more further heteroatoms, form a 4-membered to 12-membered heterocyclic ring, R$^2$ represents cyano, alkoxycarbonyl, acyl, alkylsulphonyl or arylspulphonyl, the four last-mentioned groups being optionally substituted, or represents an amide or thioamide group, comprising the radical CO—NR$^6$R$^7$ or CS—NR$^6$R$^7$, wherein R$^6$ represents hydrogen or alkyl and R$^7$ represents alkyl, cycloalkyl or optionally substituted phenyl, or R$^2$ and R$^3$, together with the connecting carbon atom, represent an α-cycloalkanone ring system with 5 to 7 carbon atoms, which can be optionally substituted, which possess fungicidal properties.

7 Claims, No Drawings

COMBATING FUNGI WITH 2-METHYLENE-3-SUBSTITUTED-4,5-BIS-TRIFLUORO-METHYL IMINO-THIAZOLIDINES

The present invention relates to and has for its objects the provision of particular new 2-methylene-3-substituted-4,5-bis-trifluoromethylimino-thiazolidines which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

As is known, zinc ethylene-bis-dithiocarbamate is used to a large extent for combating fungi which are harmful to plants (see Phytopathology 33, 1113 (1943)), but the action of this standard preparation is not always completely satisfactory. 4,5-Bis-trifluoromethyliminothiazolidines, which are likewise known, also have a good fungicidal activity (see, in this context, U.S. Pat. No. 3,895,020), but in this case also the action displayed is not always completely satisfactory when low amounts are used.

The present invention now provides, as new compounds, the trifluoromethylimino-thiazolidine derivatives of the general formula

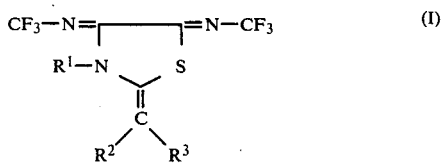

in which

R$^1$ represents optionally substituted alkyl, optionally substituted alkenyl, optionally substituted alkynyl, optionally substituted cycloalkyl, optionally substituted aryl, aralkyl, it being possible for the last-mentioned group to be substituted on the aryl radical, or an amino group —NR$^4$R$^5$, wherein R$^4$ and R$^5$, which may be identical or different, each represent optionally substituted alkyl, or R$^4$ and R$^5$, together with the connecting nitrogen atom and optionally one or more further hetero-atoms, such as oxygen, sulphur or nitrogen, form a 4-membered to 12-membered heterocyclic ring, R$^2$ represents hydrogen, cyano, alkoxycarbonyl or acyl and R$^3$ represents cyano, alkoxycarbonyl, acyl, alkylsulphonyl or arylsulphonyl, the four last-mentioned groups being optionally substituted, or represents an amide or thioamide group, comprising the radical CO—NR$^6$R$^7$ or CS—NR$^6$R$^7$, wherein R$^6$ represents hydrogen or alkyl and R$^7$ represents alkyl, cycloalkyl or optionally substituted phenyl, or R$^2$ and R$^3$, together with the connecting carbon atom, represent an α-cycloalkanone ring system with 5 to 7 carbon atoms, which can be optionally substituted.

Preferably, R$^1$ represents a straight-chain or branched alkyl, alkenyl or alkynyl radical with up to 6 (especially up to 4) carbon atoms, which radical can be substituted by cyano or an alkoxy or alkylmercapto group with in either case up to 3 carbon atoms, or represents cycloalkyl with 5 to 6 carbon atoms, which is optionally substituted by alkyl with 1 to 3 carbon atoms, or represents aryl with up to 10 carbon atoms or aralkyl with up to 10 carbon atoms in the aryl part and 1 or 2 carbon atoms in the alkyl part, the aryl radicals mentioned being optionally substituted by halogen, cyano, nitro or alkyl, alkoxy or alkylmercapto with in each case up to 3 carbon atoms, or represents an amino group —NR$^4$R$^5$, wherein R$^4$ and R$^5$, which may be identical or different, each represent straight-chain or branched alkyl with 1 to 12 (especially 1 to 4) carbon atoms, or R$^4$ and R$^5$ together with the connecting nitrogen atom and optionally one or more further heteroatoms selected from oxygen, sulphur and nitrogen, form a heterocyclic ring with 5 to 7 ring atoms;

R$^2$ represents hydrogen, cyano, alkoxycarbonyl with up to 4 carbon atoms in the alkyl part or an acyl group with a total of up to 10 (especially up to 4) carbon atoms; and R$^3$ represents cyano or alkoxycarbonyl with up to 4 carbon atoms in the alkyl part and which can be optionally substituted by an alkoxy or alkylmercapto group with up to 3 carbon atoms, or represents an acyl group with a total of up to 10 carbon atoms (especially up to 6 carbon atoms), alkylsulphonyl with up to 6 carbon atoms or arylsulphonyl with up to 10 carbon atoms in the aryl part, which aryl part is optionally substituted by alkyl with up to 3 carbon atoms and/or nitro and/or halogen, or represents an amide or thioamide group comprising the radical CO—NR$^6$R$^7$ or CS—NR$^6$R$^7$, in which R$^6$ represents hydrogen or alkyl with up to 4 carbon atoms and R$^7$ represents alkyl with up to 6 carbon atoms, cycloalkyl with 5 or 6 carbon atoms or phenyl, which phenyl can be substituted by halogen, nitro or alkyl, alkoxy or alkylmercapto with in each case up to 4 carbon atoms; or R$^2$ and R$^3$, together with the connecting carbon atom, represent an α-cycloalkanone ring system with 5 or 6 carbon atoms (for example an α-cyclopentanone or α-cyclohexanone ring system) which is optionally substituted by alkyl with up to 3 carbon atoms.

Surprisingly, the trifluoromethylimino-thiazolidine derivatives according to the invention have a more powerful fungicidal activity than the substances known from the state of the art. The compounds according to the invention thus represent an enrichment of the art.

The invention also provides a process for the production of a trifluoromethylimino-thiazolidine derivative of the formula (I) in which a thioamide of the general formula (shown in the reactive enthiol form)

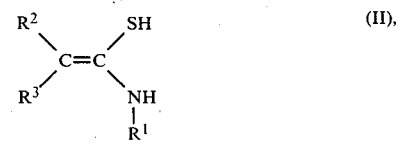

in which R$^1$, R$^2$ and R$^3$ have the meanings stated above, is reacted with bis-trifluoromethylimino-oxalic acid difluoride, of the formula

in the presence of a hydrogen fluoride-acceptor.

If (N-benzyl)-malonic acid thioamide methyl ester and bis-trifluoromethylimino-oxalic acid difluoride are used as starting materials, the course of the reaction can be represented by the equation which follows:

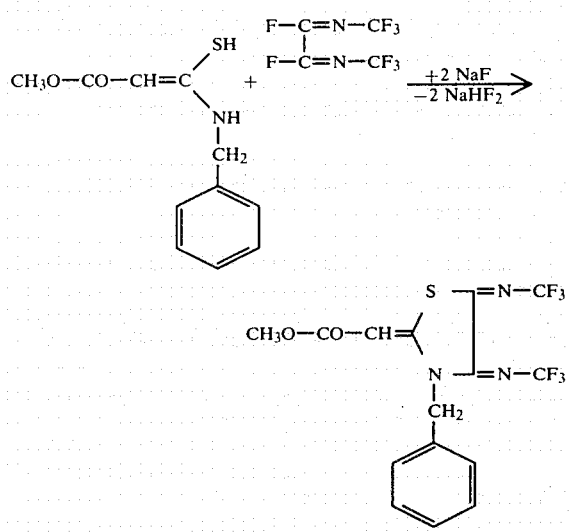

The thioamides of the formula (II), or (in cases in which $R^1$ represents an optionally substituted amino group) thiohydrazides, are known compounds and can be prepared by processes which are generally known. Thus, for example, malonic acid dithioamides are obtained by reacting malonic acid amides with phosphorus pentasulphide (Ber. dtsch. chem. Ges. 39, B 298 (1906)) or by deacylating acetylacetone with 2 moles of an isothiocyanate per mole of acetylacetone (J. prakt. Chem. 30, 63 (1965), abstracted in Chem. Abstracts 64, 3411 d (1966), and Liebigs Ann. Chem. 695, 49 (1966)). Acetoacetic acid thioamides are obtained by reacting acetylacetone with, per mole, one mole of isothiocyanate (J. Am. Chem. Soc. 42, 1055 (1920) and Z. Chem. 16, 452 (1976)). According to the same equation, acetoacetamides also react with aromatic isothiocyanates to give (N-aryl)-malonic acid thioamides (J. prakt. Chem. 34, 251 (1966)). (N-Aryl)-malonic acid thioamide esters can accordingly also be prepared from acetoacetates and aromatic isothiocyanates (Z. Chem. 5, 104 (1965), abstracted in Chem. Abstracts 63, 5546 d (1965), and Liebigs Ann. Chem. 695, 49 (1966)). (N-Alkyl)-malonic acid thioamide esters and thiohydrazide esters can be obtained in good yield in a simple manner by reacting the asymmetric dithiomalonic esters (Suomen Kemistilehti B 17, 28 (1944)) with primary aliphatic amines or 1,1-disubstituted hydrazines (see Zh. Org. Khim. 11, 1192 (1975)). Benzoylacetic acid thioamides or cycloalkan-2-one-thiocarboxylic acid anilides can be synthesized by acylation of α-morpholinostyrene or 1-morpholino-cycloalk-1-enes with isothiocyanates and subsequent acid hydrolysis (Chem. Ber. 95, 926 (1926), abstracted in Chem. Abstracts 57, 4654 (1962)). Finally, cyanoacetic acid thioanilides are obtained by acylation of cyanoacetates with aryl isothiocyanates and subsequent saponification and decarboxylation of the adducts (Zh. Obsh. Khim. 32, 2248 (1962), abstracted in Chem. Abstracts 58, 7863 f (1963); Khim. Get. Soed. 1, 698 (1965), abstracted in Chem. Abstracts 64, 9702 c (1966); and Khim. Get. Soed. 3, 713 (1967), abstracted in Chem. Abstracts 68, 49503 j (1968)).

Those secondary thioamides which have a mobile hydrogen atom in the α-position are advantageously used for carrying out the process according to the invention. The thioamides formally react in the enthiol form, such as has been shown in formula (II).

The bis-trifluoromethylimino-oxalic acid difluoride of the formula (III), also called perfluoro-2,5-diazahexa-2,4-diene, which is also used as a starting material, is known (see J. Am. Chem. Soc. 89, 5007 (1967) or U.S. Pat. No. 3,660,511).

In the preparative process of the present invention, the customary organic solvents and diluents can be used as diluents, especially hydrocarbons, for example benzine, toluene and cyclohexane; nitriles, for example acetonitrile or propionitrile; chlorinated hydrocarbons, such as methylene chloride, chloroform and chlorobenzene; or ketones, for example acetone. The reaction is preferably carried out in acetone or acetonitrile.

The customary acid-binding agents can be used as the hydrogen fluoride binding agent. Alkali metal carbonates, alkali metal bicarbonates and tertiary amines, such as triethylamine, dimethylaniline or pyridine, can be used as such agents. However, alkali metal fluorides, for example sodium fluoride, are particularly preferably employed for bonding the hydrogen fluoride liberated.

The reaction temperatures can be varied within a substantial range. In general, the reaction is carried out at from $-50°$ to $+120°$ C., preferably from $-30°$ to $+90°$ C.

For carrying out the process according to the invention, 1 mole of bis-trifluoromethylimino-oxalic acid difluoride of the formula (III) is preferably employed per mole of the compound of the formula (II). The alkali metal fluoride, or another hydrogen fluoride-acceptor, is employed in an approximately 2 to 4 molar amount. Amounts up to about 20% less or more than the proportions indicated can be used without substantially lowering the yield. The bis-trifluoromethylimino-oxalic acid difluoride is appropriately added dropwise to a suspension consisting of the thioamide, the organic solvent and the hydrogen fluoride-acceptor, the mixture advantageously being initially cooled with a cooling bath. After the reaction has ended (for example after a period of 30 minutes to 24 hours at room temperature) the hydrogen fluoride formed is filtered off, the filtrate is concentrated and the crystalline residue is purified by recrystallization. However, after the reaction has ended, it is also possible to pour the resulting mixture, or the filtered solution, into ice-water and to filter off and if appropriate recrystallize the residue obtained.

A variant of the process for the preparation of a compound according to the invention consists in reacting a suitable thioamide with N,N'-bis-(trifluoromethyl)-tetrafluoroethylene-1,2-diamine, which is known, in the presence of a hydrogen fluoride-acceptor in the temperature range between $-50°$ and $+120°$ C.

In this case, 1 mole of N,N'-bis-(trifluoromethyl)-tetrafluoroethylene-1,2-diamine and 4–5 moles of the hydrogen fluoride-acceptor are advantageously employed per mole of thioamide (this process variant is carried out analogously to the method disclosed in DT-OS (German Published Specification ) No. 2,210,882).

The active compounds according to the invention exhibit a powerful fungitoxic action. They do not damage crop plants in the concentrations required for combating fungi. For these reasons, they are suitable for use as plant protection agents for combating fungi. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or which attack the plants through the soil, as well as against seed-borne pathogens.

The compounds have a good activity against *Fusicladium dendriticum*, the apple scab causative organism, against *Phytophthora infestans*, the potato blight and rot causative organism, and against *Pyricularia oryzae* the causative organism of rice blast, and against *Pellicularia sasakii*, the causative organism of sheath blight of rice.

However, the compounds according to the invention are also active against other fungi which attack rice plants or other cultivated plants, such as, for example, against *Mycosphaerella musicola*, *Verticillium alboatrum* and *Phialophora cinerescens*, and against the bacterium *Xanthomonas oryzae*.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds can be used as such or in the form of their formulations or the use forms prepared therefrom, such as ready-to-use solutions, emulsifiable concentrates, emulsions, suspensions, wettable powders, pastes, soluble powders, dusting agents and granules. They are used in the customary manner, for example by spraying, atomizing, misting, dusting, scattering, fumigating, gassing, watering, dressing or encrusting.

The concentrations of active compound in the ready-to-use formulations can be varied within substantial ranges. They are, in general, from 0.0001 to 10%, preferably from 0.01 to 1%.

The compounds according to the invention also have an acaricidal action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is shown in the following illustrative example:

EXAMPLE 1

(a) Preparation of the precursor 160 ml of acetylacetone, 400 ml of absolute ether and 23 g of finely cut sodium were stirred at room temperature for 2.5 hours. 135 g of phenyl isothiocyanate were then added dropwise at room temperature and the mixture was subsequently stirred at room temperature for 60 hours. 120 ml of absolute methanol were then added dropwise and the mixture was left to stand at room temperature for 20 hours. It was taken up in 200 ml of ice-water, to which 200 ml of 10% strength sodium hydroxide solution had been added, the ether was separated off and the aqueous solution was neutralized with 10% strength hydrochloric acid at about 0° C., while cooling. The precipitate was filtered off, washed with water and dried and recrystallized from carbon tetrachloride. 157 g of acetoacetic acid thioanilide of melting point 56°-58° C. were obtained.

(b) 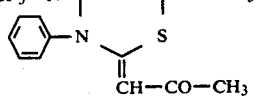 (1)

23 g (about 0.1 mol) of bis-trifluoromethyliminooxalic acid difluoride were added dropwise to a suspension of 19.3 g (0.1 mol) of acetoacetic acid thioanilide and 15 g (0.36 mol) of sodium fluoride in 120 ml of acetone at about 5° to 15° C., while cooling with ice and stirring. The mixture was stirred at room temperature for 2 hours and the precipitate was filtered off and rinsed with warm acetonitrile. The product phase was then discharged onto ice and the solid was filtered off and rinsed with a large amount of water, and the residue was recrystallized from ethyl alcohol. 32 g of 2-acetyl-methylene-3-phenyl-4,5-bis-trifluoromethyliminothiazolidine of melting point 189°-191° C. were obtained, that is to say 84% of theory.

The compounds which follow, of the general formula

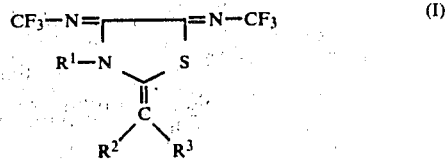 (I)

where obtained in a corresponding manner:

| Compound No. | $R^1$ | $R^2$ | $R^3$ | Melting point (°C.) |
|---|---|---|---|---|
| 2 | O(CH₂CH₂)₂N— (morpholino) | H | CO—OCH₃ | 165–167 |
| 3 | C₆H₅—CH₂— (benzyl) | H | CO—OCH₃ | 164–165 |
| 4 | C₆H₅— | CO—OC₂H₅ | CO—OC₂H₅ | 220–222 |
| 5 | C₆H₅— | H | CO—NH—C₆H₅ | 224–225 |
| 6 | C₆H₅— | CN | SO₂—C₆H₄—CH₃ | 286–287 |
| 7 | C₆H₅— | CN | CO—OC₂H₅ | 205–206 |
| 8 | C₆H₅— | H | CS—NH—C₆H₅ | 207 |
| 9 | 3,4-Cl₂-C₆H₃— | H | CO—OCH₃ | 151–152 |
| 10 | 4-Cl-C₆H₄— | H | CO—OCH₃ | 167–168 |

-continued
| Compound No. | R¹ | R² | R³ | Melting point (°C.) |
|---|---|---|---|---|
| 11 | 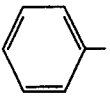 | H | 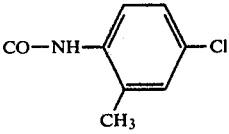 | 226–227 |
| 12 |  | H | 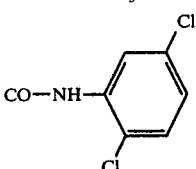 | 196–197 |
| 13 | 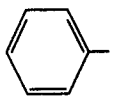 | H | 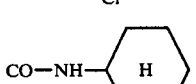 | 224–225 |
| 14 | 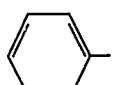 | H | 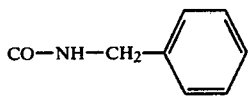 | 237–238 |
| 15 |  | H | CO—OCH₃ | 176–177 |
| 16 |  | H | CO—OC₂H₅ | 214–215 |
| 17 | 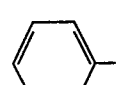 | H | CN | 218–219 |
| 18 | 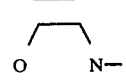 | H | CO—OC₂H₅ | 193–194 |
| 19 | 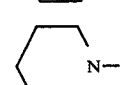 | H | CO—OC₂H₅ | 167–168 |
| 20 | 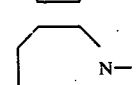 | H | CO—OCH₃ | 136–137 |
| 21 | 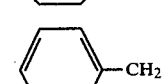 | H | CO—OC₂H₅ | 166–167 |
| 22 | 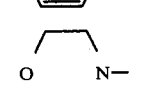 | H | CO—OC₂H₄OCH₃ | 128–130 |
| 23 | 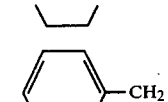 | H | CO—OC₂H₄OCH₃ | 146–147 |
| 24 | 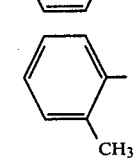 | H | CO—OCH₃ | 227–228 |

-continued

| Compound No. | R¹ | R² | R³ | Melting point (°C.) |
|---|---|---|---|---|
| 25 | 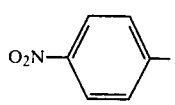 4-O₂N-C₆H₄- | H | CO—OCH₃ | 217–218 |
| 26 | 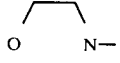 morpholino | H | CO—OC₃H₇-n | 127–128 |
| 27 | 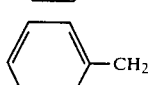 C₆H₅-CH₂- | H | CO—OC₃H₇-n | 137–138 |
| 28 | 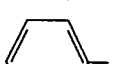 C₆H₅- | H | 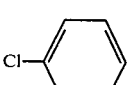 CO—C₆H₅ | 203–204 |
| 29 | 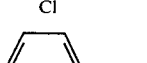 2,3-Cl₂-C₆H₃- | H | 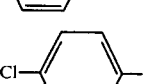 CO—C₆H₅ | 187–188 |
| 30 | 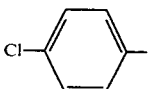 C₆H₅-CH₂- | H | 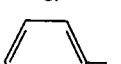 CO—C₆H₅ | 200–202 |
| 31 | 4-Cl-C₆H₄- | H | CO—CH₃ | 220–221 |
| 32 | 3,4-Cl₂-C₆H₃- | H | CO—CH₃ | 202–203 |
| 33 | C₆H₅- | | CH₂—CH₂—CH₂—CH₂—CO | 157–158 |
| 34 | C₆H₅- | | CH₂—CH₂—CH₂—CO | 169–170 |
| 35 | 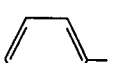 2-CH₃-C₆H₄- | | CH₂—CH₂—CH₂—CH₂—CO | 162–163 |

The activity of the compounds of this invention is illustrated by the following examples, wherein the compounds according to the present invention are each identified by the number (given in brackets) from Example 1 hereinabove.

EXAMPLE 2

Agar plate test

Nutrient medium used:
  20 parts by weight of agar-agar
  200 parts by weight of potato decoction
  5 parts by weight of malt
  15 parts by weight of dextrose
  5 parts by weight of peptone
  2 parts by weight of disodium hydrogen phosphate
  0.3 part by weight of calcium nitrate Composition of the solvent mixture:
  0.19 part by weight of acetone or dimethylformamide
  0.01 part by weight of emulsifier (alkylaryl polyglycol ether)
  1.80 parts by weight of water Ratio of solvent mixture to nutrient medium:
  2 parts by weight of solvent mixture
  100 parts by weight of agar nutrient medium The amount of active compound required for the desired active compound concentration in the nutrient medium was mixed with the stated amount of solvent mixture. The concentrate was thoroughly mixed, in the stated proportion, with the liquid nutrient medium (which had been cooled to 42 deg.C.) and was then poured into Petri dishes of 9 cm diameter. Control plates to which the preparation had not been added were also set up.

When the nutrient medium had cooled and solidified, the plates were inoculated with the species of organisms stated hereinbelow and incubated at about 21 deg.C.

Evaluation was carried out after 4–10 days, dependent upon the speed of growth of the organisms. When evaluation was carried out the radial growth of the organism on the treated nutrient media was compared with the growth on the control nutrient medium.

The action against the species of fungi *Colletotrichum coffeanum, Cochliobolus miyabeanus, Verticillium alboatrum, Pyricularia oryzae, Phialophora cinerescens, Mycosphaerella musicola* and *Pellicularia sasakii* and against the bacterium *Xanthomonas oryzae* was tested.

Evaluation of the test showed that, for example, the following compounds exhibited a superior action compared with the compounds mentioned in the prior art: compounds (2), (15), (17), (19), (20) and (33).

EXAMPLE 3

Pyricularia and Pellicularia test
Solvent: 11.75 parts by weight of acetone
Dispersing agent: 0.75 parts by weight of alkylaryl polyglycol ether
Water: 987.50 parts by weight The amount of active compound required for the desired concentration of active compound in the spray liquid was mixed with the stated amount of the solvent and of the dispersing agent and the concentrate was diluted with the stated amount of water.

Rice plants about 2–4 weeks old were sprayed with the spray liquid until dripping wet. The plants remained in a greenhouse at temperatures of 22 to 24 deg.C. and a relative atmospheric humidity of about 70% until they were dry. Thereafter, the plants were inoculated with an aqueous suspension of 100,000 to 200,000 spores/ml of *Pyricularia oryzae* and placed in a chamber at 24 to 26 deg.C. and 100% relative atmospheric humidity.

Other rice plants, which had been sprayed and dried in the above-described manner, were infected with a culture of *Pellicularia sasakii* grown on malt agar and were set up at 28 to 30 deg.C. and 100% relative atmospheric humidity.

5 to 8 days after the inoculation, the infection of all the leaves present at the time of inoculation with *Pyricularia oryzae* was determined as a percentage of the untreated but also inoculated control plants.

In the case of the plants infected with *Pellicularia sasakii*, the infection at the leaf sheaths after the same time was determined, again in relation to the untreated but infected control.

Evaluation of the tests showed that, for example, the following compounds exhibited a superior action compared with the compounds mentioned in the prior art: compounds (2), (3), (1), (15), (17), (19), (20), (33) and (35).

EXAMPLE 4

Phytophthora test (tomato)/protective
Solvent: 4.7 parts by weight of acetone
Emulsifier: 0.3 part by weight of alkylaryl polyglycol ether
Water: 95 parts by weight The amount of the active compound required for the desired concentration of the active compound in the spray liquid was mixed with the stated amount of solvent and the concentrate was diluted with the stated amount of water which contained the stated additions.

Young tomato plants with 2 to 4 foliage leaves were sprayed with the spray liquid until dripping wet. The plants remained in a greenhouse for 24 hours at 20 deg.C. and at a relative atmospheric humidity of 70%. The tomato plants were then inoculated with an aqueous spore suspension of *Phytophthora infestans*. The plants were brought into a moist chamber with an atmospheric humidity of 100% and a temperature of 18–20 deg.C.

After 5 days the infection of the tomato plants was determined.

Evaluation of the test showed that, for example, the following compounds exhibited a superior action compared with the compounds mentioned in the prior art: compounds (1), (9), (34) and (24).

EXAMPLE 5

Fusicladium test (apple)/protective
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Young apple seedlings in the 4–6 leaf stage were sprayed with the spray liquid until dripping wet. The plants remained in a greenhouse for 24 hours at 20 degrees C. and at a relative atmospheric humidity of 70%. They were then inoculated with an aqueous conidium suspension of the apple scab causative organism (*Fusicladium dendriticum*) and incubated for 18 hours in a humidity chamber at 18–20 degrees C. and at a relative atmospheric humidity of 100%.

The plants were then brought into a greenhouse again for 14 days.

15 days after inoculation, the infection of the seedlings was determined.

Evaluation of the test showed that, for example, the following compounds exhibited a superior action compared with the prior art: compounds (1), (9), (10), (15), (33), (34) and (24).

EXAMPLE 6

Shoot treatment test/cereal rust
(leaf-destructive mycosis)/protective

To produce a suitable preparation of active compound, 0.25 part by weight of active compound was taken up in 25 parts by weight of dimethylformamide and 0.06 part by weight of alkylaryl polyglycol ether and then 975 parts by weight of water are added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20 deg.C. and 100% relative atmospheric humidity.

After 10 days' dwell time of the plants at a temperature of 20 deg.C. and 80-90% atmospheric humidity, the occurrence of rust pustules on the plant was evaluated. The degree of infection was expressed as a percentage of the infection of the untreated control plants. The more active the compound, the lower was the degree of rust infection.

Evaluation of the test showed that, for example, the following compounds exhibited a superior action compared with the prior art: compounds (2), (3), (1), (9), (10), (15), (16), (17), (18), (19), (20), (33), (22), (34), (24), (25), (26) and (35).

EXAMPLE 7

Shoot treatment test/powdery mildew of cereals (leaf-destructive mycosis)/protective To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis* var. *hordei*.

After 6 days' dwell time of the plants at a temperature of 21-22 deg.C. and 80-90% atmospheric humidity the occurrence of mildew pustules on the plants was evaluated. The degree of infection was expressed as a percentage of the infection of the untreated control plants. The more active the compound, the lower was the degree of mildew infection.

Evaluation of the test showed that, for example, compound (34) exhibited a superior action compared with the compounds mentioned in the prior art.

EXAMPLE 8

Seed dressing test/bunt of wheat (seed-borne mycosis)

To produce a suitable dry dressing, the active compound was extended with a mixture of equal parts by weight of talc and kieselguhr to give a finely powdered mixture with the desired concentration of the active compound.

Wheat seed was contaminated with 5 g of the chlamydospores of *Tilletia caries* per kg of seed. To apply the dressing, the seed was shaken with the dressing in a closed glass flask. The seed, on moist loam under a cover of a layer of muslin and 2 cm of moderately moist compost soil, was exposed to optimum germination conditions for the spores for 10 days at 10 deg. C. in a refrigerator.

The germination of the spores on the wheat grains, each of which was contaminated with about 100,000 spore, was subsequently determined microscopically. The smaller the number of spores which had germinated, the more effective was the active compound.

Evaluation of the test showed that, for example, the following compounds exhibited a superior action, compared with the compounds mentioned in the prior art: compounds (1), (17) and (22).

It will be appreciated that the instant specification and examples are set forth by way of illustration and not limitation, and that various modifications and changes may be made without departing from the spirit and scope of the present invention.

What is claimed is:

1. A compound of the formula

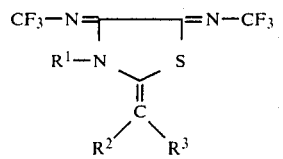

in which
R¹ represents an alkyl, alkenyl or alkynyl radical with up to 6 carbon atoms, which radical can be substituted by cyano or an alkoxy or alkylmercapto group with in either case up to 3 carbon atoms, or represents cycloalkyl with 5 to 6 carbon atoms, which is optionally substituted by alkyl with 1 to 3 carbon atoms, or represents aryl with up to 10 carbon atoms or aralkyl with up to 10 carbon atoms in the aryl part and 1 or 2 carbon atoms in the alkyl part, the aryl radicals mentioned being optionally substituted by halogen, cyano, nitro or alkyl, alkoxy or alkylmercapto with in each case up to 3 carbon atoms, or represents an amino group —NR⁴R⁵, wherein
R⁴ and R⁵ each independently represents alkyl with 1 to 12 carbon atoms or, together with the connecting nitrogen atom and optionally one or more further hetero-atoms selected from oxygen, sulphur and nitrogen, form a heterocyclic ring with 5 to 7 ring atoms,
R² represents hydrogen, cyano or an acyl group with a total of up to 10 carbon atoms, and
R³ represents cyano, or represents an acyl group with a total of up to 10 carbon atoms, alkylsulphonyl with up to 6 carbon atoms or arylsulphonyl with up to 10 carbon atoms in the aryl part, which aryl part is optionally substituted by alkyl with up to 3 carbon atoms and/or nitro and/or halogen, or represents an amide or thioamide group comprising the radical CO—NR⁶R⁷ or CS—NR⁶R⁷, in which
R⁶ represents hydrogen or alkyl with up to 4 carbon atoms, and
R⁷ represents alkyl with up to 6 carbon atoms, cycloalkyl with 5 or 6 carbon atoms or phenyl, which phenyl can be substituted by halogen, nitro or alkyl, alkoxy or alkylmercapto with in each case up to 4 carbon atoms, or
R² and R³, together with the connecting carbon atom, represent an α-cycloalkanone ring system with 5 or 6 carbon atoms which is optionally substituted by alkyl with up to 3 carbon atoms.

2. A compound according to claim 1, wherein such compound is 2-acetyl-methylene-3-phenyl-4,5-bis-trifluoromethylimino-thiazolidine of the formula

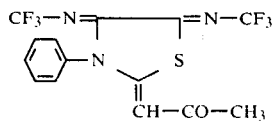

3. A compound according to claim 1, wherein such compound is 2-α-ketocyclopentylidene-3-phenyl-4,5-bis-trifluoro-methylimino-thiazolidine of the formula

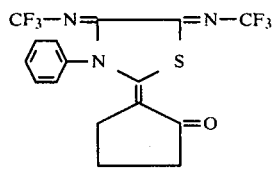

4. A compound according to claim 1, wherein such compound is 2-α-ketocyclohexylidene-3-o-tolyl-4,5-bis-trifluoro-methylimino-thiazolidine of the formula

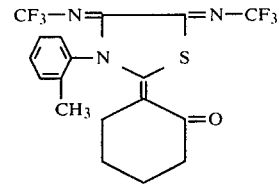

5. A fungicidal composition containing as active ingredient a fungicidally effective amount of a compound according to claim 1 in admixture with a diluent.

6. A method of combating fungi which comprises applying to the fungi, or to a habitat thereof, a fungicidally effective amount of a compound according to claim 1.

7. The method according to claim 6, in which said compound is
2-acetyl-methylene-3-phenyl-4,5-bis-trifluoromethylimino-thiazolidine,
2-α-ketocyclopentylidene-3-phenyl-4,5-bis-trifluoromethylimino-thiazolidine, or
2-α-ketocyclohexylidene-3-o-tolyl-4,5-bis-trifluoromethylimino-thiazolidine.

* * * * *